US009114225B1

(12) United States Patent  
Roberts et al.

(10) Patent No.: US 9,114,225 B1  
(45) Date of Patent: *Aug. 25, 2015

(54) MEMBRANE OXYGEN HUMIDIFIER

(71) Applicant: CORAD Healthcare, Inc., White Bear Lake, MN (US)

(72) Inventors: Keith A. Roberts, White Bear Lake, MN (US); Jeff Helget, New Brighton, MN (US)

(73) Assignee: Corad Healthcare, Inc., White Bear Lake, MN (US)

( * ) Notice: Subject to any disclaimer, the term of this patent is extended or adjusted under 35 U.S.C. 154(b) by 335 days.

This patent is subject to a terminal disclaimer.

(21) Appl. No.: 13/675,974

(22) Filed: Nov. 13, 2012

Related U.S. Application Data

(63) Continuation-in-part of application No. 13/592,655, filed on Aug. 23, 2012, now Pat. No. 8,307,826, and a continuation-in-part of application No. 12/402,288, filed on Mar. 11, 2009, now Pat. No. 8,307,825.

(60) Provisional application No. 61/082,247, filed on Jul. 21, 2008.

(51) Int. Cl.  
*A61M 16/16* (2006.01)

(52) U.S. Cl.  
CPC ..................... *A61M 16/16* (2013.01)

(58) Field of Classification Search  
CPC ............ A61M 16/16; F16B 2/20; F16B 2/22; F16B 2/24; F16B 2/241; F16B 2/243; F16B 2/248; F16B 7/0433  
USPC ............. 128/201.13, 203.12, 203.15–203.17; 261/100–104; 96/7–10; 95/52, 117  
See application file for complete search history.

(56) References Cited

U.S. PATENT DOCUMENTS

| | | | | |
|---|---|---|---|---|
| 3,154,281 A | * | 10/1964 | Frank | 248/201 |
| 4,038,190 A | * | 7/1977 | Baudet et al. | 210/321.81 |
| 4,075,100 A | * | 2/1978 | Furuta et al. | 210/266 |
| 4,379,539 A | * | 4/1983 | Rion et al. | 248/371 |
| 5,211,728 A | * | 5/1993 | Trimmer | 95/47 |
| 6,558,451 B2 | | 5/2003 | McCombs et al. | |
| 6,783,008 B2 | * | 8/2004 | Zha et al. | 210/485 |
| 6,951,611 B2 | * | 10/2005 | Dannenmaier et al. | 210/321.89 |

(Continued)

FOREIGN PATENT DOCUMENTS

JP          2-99113         4/1990

OTHER PUBLICATIONS

Burioka et al. (Burioka et al., Membrane Humidifier That Does Not Require Addition of Water, Yonago Acta medica, 1999; 42:185-188.*

Burioka et al., "Efficacy of a Newly Developed Pressure Swing Adsorption Type Oxygen Concentrator with Membrane Humidifier: Comparison with Conventional Oxygen Concentrator with Bubble Water Humidifier", Internal Medicine, 36(12):861-864 (Dec. 1997).

*Primary Examiner* — Lynne Anderson  
*Assistant Examiner* — Kathryn E Ditmer  
(74) *Attorney, Agent, or Firm* — Dicke, Billig & Czaja, PLLC

(57) ABSTRACT

A membrane oxygen humidifier that is associated with a gas source for increasing humidity of the gas. The membrane oxygen humidifier includes an enclosure, a membrane unit and a humidification source. The enclosure includes an inlet port and an outlet port. The membrane unit is removably mounted in the enclosure to extend between the inlet port and the outlet port. The humidification source in communication with the enclosure and the membrane unit.

15 Claims, 8 Drawing Sheets

(56) References Cited

U.S. PATENT DOCUMENTS

| | | |
|---|---|---|
| 7,156,375 B2* | 1/2007 | Yazawa .................. 261/23.1 |
| 7,331,342 B2 | 2/2008 | Spearman et al. |
| 7,428,902 B2 | 9/2008 | Du et al. |
| 7,753,991 B2 | 7/2010 | Kertzman |

| | | | |
|---|---|---|---|
| 2002/0024155 A1* | 2/2002 | Kusano et al. ............ 261/104 |
| 2004/0144712 A1* | 7/2004 | Stroh et al. ............ 210/321.89 |
| 2005/0072425 A1* | 4/2005 | Spearman et al. ....... 128/204.17 |
| 2006/0113235 A1* | 6/2006 | Strohm et al. ............ 210/232 |
| 2007/0210463 A1* | 9/2007 | Koenig et al. ............ 261/100 |

* cited by examiner

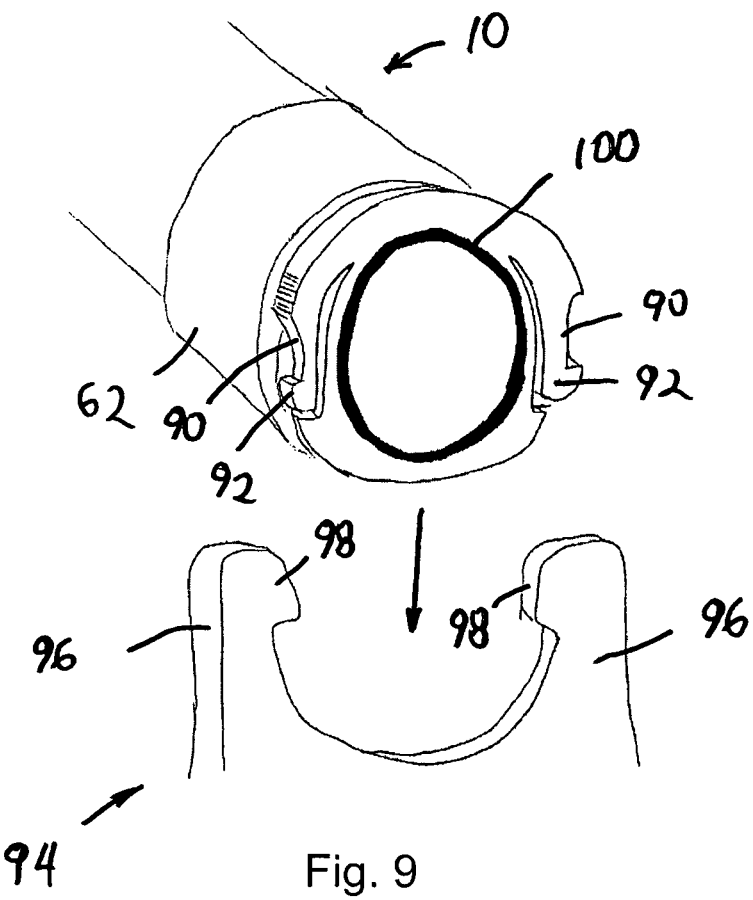
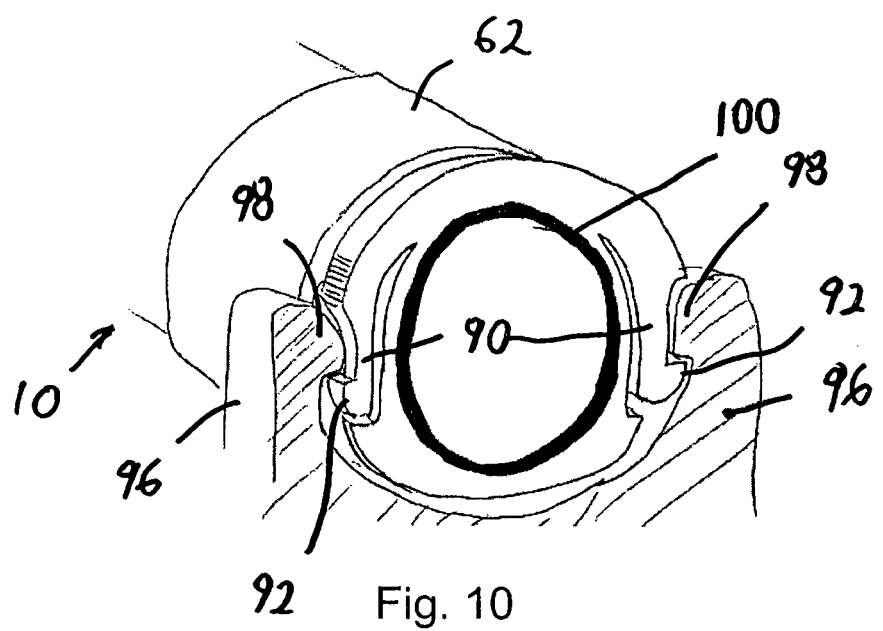
Fig. 9
Fig. 10

MEMBRANE OXYGEN HUMIDIFIER

REFERENCE TO RELATED APPLICATION

This application is a continuation-in-part of U.S. application Ser. No. 13/592,655, filed Aug. 23, 2012, and U.S. application Ser. No. 12/402,288, filed Mar. 11, 2009, which both claim priority to U.S. Provisional application No. 61/082,247, filed Jul. 21, 2008, the contents of which are incorporated herein by reference.

FIELD OF THE INVENTION

The invention relates generally to systems for providing oxygen to persons. More particularly, the invention relates to systems of providing breathable humidified oxygen gas to a patient.

BACKGROUND OF THE INVENTION

The method to produce oxygen from oxygen concentrators using pressure swing adsorption is widely known in the art, see Spearman et al., U.S. Pat. No. 7,331,342 and McCombs et al., U.S. Pat. No. 6,558,451. Oxygen concentrators produce a high level of oxygen of approximately 95% at flow rates approximately 1-10 liters per minute (lpm). There are approximately 2 million oxygen concentrators in use in America.

Oxygen concentrators that utilize pressure swing adsorption to increase the oxygen concentration cause the moisture level to be very low. In fact, the oxygen can be so dry to a patient that the patient can suffer bloody noses and dry lungs due to the rapid evaporation of fluid from tissue cells within the nasal passage way and lungs. To combat the problem of dry gas being delivered to the patient, health care providers will do one of two things to deliver humidified gases to their patients, each of which has shortcomings.

One technique to humidify the oxygen is to connect the patient oxygen port outside of the concentrator to a water bubbler through which the oxygen bubbles and adsorbs water that is subsequently delivered to the patient at relatively high levels of humidity, approximately 50%-90%. This high level of humidity is beneficial to the patient and provides comfort to the patient.

Bacteria however, can grow within the humidifier itself, thereby jeopardizing the patient's safety. Additionally, the bubblers on a humidifier are recommended to be changed quite frequently by the health care provider. These bubblers are not reimbursed and are paid for out of the health care provider's pocket. This can be quite costly for a healthcare provider.

Another technique to provide humidification is through membrane gas humidifiers. Porous Media's HUMIDIFLOW membrane gas humidifier, which was the subject of U.S. Pat. No. 7,331,342, provides humidification to the patient without using water bubblers, but rather using a hollow fiber membrane having a high selectivity of water over nitrogen and oxygen.

This device is installed on the upstream side of the air compressor in the oxygen concentrator and plumbed to flow atmospheric air from the air compressor across one side of the membranes and oxygen from the downstream side of the molecular sieve beds across the other side to induce a gradient such that the water vapor in the atmosphere on the one side of the fibers transfers to the dry oxygen on the other side of said hollow fiber membrane to a level of humidity that is close to that of the room air.

Porous Media teaches installing the HUMIDIFLOW membrane gas humidifier inside the oxygen concentrator: "In one embodiment of the present invention, the membrane device is installed in the oxygen concentrator such that the membrane device engages a stream of ambient air prior to the compression of the ambient air by a compressor while an oxygen-enriched gas engages the membrane device after the oxygen-enriched gas has engaged a regulator and needle valve."

"In an alternative embodiment of the present invention, the membrane device is installed in an oxygen concentrator such that the membrane device engages the stream of ambient air after compression of the ambient air by the compressor while the oxygen-enriched gas engages the membrane device prior to the engagement of the oxygen-enriched gas with the gas regulator" and "More specifically, since membrane devices used in oxygen concentrators are usually installed downstream of the compressor", and "A second embodiment of the present invention involves installing the membrane device in an oxygen concentrator . . . " from page 3 of the provisional patent.

There are many problems with the prior art inventions created by having to install the device in the inside of an oxygen concentrator. As illustrated from an instructional installation DVD for the HUMIDIFLOW membrane gas humidifier, which was purchased from a publicly available distributor of Porous Media listed on the HUMIDIFLOW website (The Aftermarket Group, OH) the following problems can be observed pertaining to the installation of the HUMIDIFLOW membrane gas humidifier. First is that the health care provider is required to remove the oxygen concentrator cabinet that is generally secured by screws to a frame on the oxygen concentrator.

Then the health care provider is required to re-plumb the original manufacturer's equipment so that the oxygen tubing is re-routed from the flow meter to the membrane and from the membrane back to the patient. Next, the health care provider must ensure that the membrane is secured to the inside of the concentrator using nylon zip ties that may come loose during transportation or if not installed properly, cause potential rattling of the membrane against other components inside of the concentrator.

In one case, the health care provider is instructed to install a custom compressor inlet filter to the inlet of the HUMIDIFLOW membrane gas humidifier. The intake filter of the HUMIDIFLOW membrane gas humidifier kits may become detached from the module and fall onto the compressor cooling fan during patient treatment. If the filter were to come in contact with the fan blades this could stop the fan from operating and cause the concentrator to overheat and interrupt the flow of oxygen to the patient.

Further, there are dozens of oxygen concentrator brands and part numbers on the market, each oxygen concentrator brand requiring a HUMIDIFLOW membrane gas humidifier with different tubing lengths and various connectors. One HUMIDIFLOW membrane gas humidifier requires a special mounting bracket that one has to mount to the top of the air compressor to secure the HUMIDIFLOW membrane gas humidifier in place.

This process requires removing a portion of the air compressor OEM's air compressor components to retrofit a particular oxygen concentrator for the HUMIDIFLOW membrane gas humidifier. As one can see, the installation of the HUMIDIFLOW membrane gas humidifier is less than ideal from an operations stand point or ease of use from the patient's perspective.

It is common for an oxygen concentrator dealer to carry multiple brands of oxygen concentrators and if this is the case, the dealer must inventory as many part numbers of HUMIDIFLOW membrane gas humidifiers as there are concentrators. It is conceivable that the healthcare provider would have to inventory up to 15 or more different HUMIDIFLOW membrane gas humidifier part numbers.

Every oxygen concentrator on the market requires that the health care provider measure and verify the oxygen concentration performance of the concentrator. This process is generally done with an oxygen sensor and can be easily measured by holding the sensor up to the oxygen flow meter. However, the oxygen sensors will only give an accurate reading of the concentrator's oxygen level output in the presence of dry gas.

Since the prior art must be installed to verify that it is not affecting the oxygen levels, one must now take another step to dry the gas that has been humidified by the membrane. The way this process is accomplished is by purchasing another in line air dryer comprised generally of PVC tubing and a desiccant.

The operator must install the in line dryer at the concentrator's outlet, dry the oxygen using the desiccant dryer and then measure the oxygen concentration of the concentrator. This desiccant dryer can have a very short life and must be either re-charged by putting in an oven, or the operator must purchase another in line dryer.

While membrane devices such as the Teijin and HUMIDIFLOW membrane gas humidifier address a need in the marketplace to provide comfortable levels of humidity without requiring liquid water when the ambient humidity is at levels of 25-30% RH, there exists an inherent problem with prior art membranes in their ability to control humidity to the patient in dry weather. As explained in the Teijin patent, the "make up" air is the ambient air that is drawn through the air compressor.

The oxygen is plumbed to the Teijin membrane humidifier and picks up the moisture from the "make up" air side of the membrane via diffusion across the membrane. If the room air is 15% RH, for example in the case of many Southwestern states in the winter months, supplemental humidification may be needed. To provide higher levels of humidity to the patient when the room RH is low, the humidifier may need to be installed near the oxygen concentrator.

To increase the humidity to the patient in dry weather, one must increase the humidity in the room at the inlet of the air compressor or "make up air" as Teijin refers to this process, using water droplets and water vapor from a room air humidifier. Most compressors installed in oxygen concentrators operate at approximately 100 lpm. Most oxygen concentrators such as Teijin's have an oxygen flow rate of approximately 5 lpm.

Both of the Teijin and Porous Media membrane humidifiers require the plumbing of the oxygen line to a port of the membrane. Both Teijin and the HUMIDIFLOW offer the use of a fan inside the oxygen concentrator to direct the airflow across the membrane.

Another membrane humidifier very similar to the Porous Media HUMIDIFLOW is mentioned in the Teijin patent. The oxygen flows on the opposite side of the fibers containing the makeup air. When a supplemental room air humidifier is installed near the inlet of one of these common membrane humidifiers, the small flow of oxygen relative to the makeup air becomes saturated with water and is delivered to the patient.

This is good for the patient because much of the oxygen will now be saturated. However, In the case of a conventional membrane such as the above mentioned membranes, much of the compressed air will also be saturated, but now entering the molecular sieve beds due to the fact that only a relatively small amount of water will be removed from the makeup air and put into the oxygen stream. This deficiency in these conventional membranes will lead to reduced sieve life.

While the above mentioned membranes are generally effective at increasing the humidity in dry weather to more comfortable levels of approximately 30% RH using a room air humidifier, for the prior art membranes to provide much more humidity than this is extremely difficult without encountering major problems for the oxygen concentrator as well as the patient's home.

In the average US household, each furnace is equipped with a blower ranging from several hundred SCFM to several thousand SCFM. This means that the air exchange in a standard 10 foot×10 foot room can be 50-200 SCFM. To compound the problem, the atmospheric air drawn by the compressor is rushing through the Teijin and HUMIDIFLOW membranes at a rate of approximately 100 lpm from the air compressor compared to the relatively small flow of 5-10 lpm for the dry oxygen plumbed on the opposite side of the fibers.

The average room air supplemental humidifier patients purchase at pharmacies and drug stores only put out several liters per minute to several SCFM of saturated humidity, which is obviously not enough to keep up with the air compressor inlet flow rate and the air exchange of the room.

This means in order to humidify a 10 foot×10 foot room to levels of high humidity over about 50%, preferably >60-80% one would literally have to line the floors of this room with humidifiers which in turn would coat every square inch of surface area of the room, including the flooring, walls, windows, books, electrical fixtures, etc. with water droplets, ultimately resulting in the growth of mold and spores.

As indicated before, the effects of this amount of water on the oxygen concentrator would be overwhelming to the sieve beds and would cause a substantial reduction in sieve life, not to mention rusting the metal and electrical components within the concentrator.

The Teijin oxygen concentrator which is subject of U.S. Pat. No. 6,669,956 utilizes a similar operational principal of the Porous Media oxygen concentrator, however it features a NAFION cationic conductive membrane that is coupled to a cathode and an anode. When an electric current is applied to the conductive membrane, it produces a higher level of humidity on the patient outlet end than the atmospheric air or "make up" air as Teijin describes it. This membrane however loses its charge over time and becomes a "passive" membrane just like the Porous Media HUMIDIFLOW membrane gas humidifier.

Teijin describes another Japanese membrane that basically accomplishes a similar "passive" humidification means as the membrane gas humidifier in JP Patent No. 2-99113. The indicated benefit of the Teijin design is that for a period of time (albeit very brief), they are able to control the level of humidity to the patient through the use of applying a higher or lower amount of current to their conductive membrane, depending upon the amount of humidity desired at the patient end.

The Burioka oxygen concentrator connects a polyimide hollow fiber (from UBE Industries, Ltd, Japan) membrane shell consisting of 4 connection ports to an air compressor and an oxygen source as described in an article entitled "Efficacy of a Newly Developed Pressure Swing Adsorption Type Oxygen Concentrator with Membrane Humidifier: Comparison with Conventional Oxygen Concentrator with Bubble Water Humidifier."

The air compressor takes compressed air and compresses the atmospheric air to between about 14 psig and 28 psig. The paper shows a chart illustrating that at approximately 20% RH room air humidity. Burioka was able to achieve 50-60%

RH in the patient gas and approximately 80% RH in the patient gas when the room was 30% RH.

However, the Burioka prototype suffers from several design deficiencies. First is that the membrane must be installed downstream of an air compressor, which is inside the oxygen concentrator. This configuration would be extremely difficult for aftermarket installations.

Since some oxygen concentrator air compressors can operate at relatively high temperatures inside the cabinet (nearly 230° F. in some cases) and the compressors can put out an extremely high amount of contamination, this configuration would expose the membrane to conditions of operation that could cause fatigue and contamination of the membranes.

Further, the Burioka design of humidification system provides the patient and the health care provider with a level of humidification that could be too high when operated continually at higher levels of room RH and leaves the patient with no choice or control over the level of humidity.

U.S. Pat. No. 7,331,342 indicates that humidity in the Burioka product is provided at a higher level than the atmospheric air and mentions two techniques to overcome over humidification by the membrane devices. First, the membrane devices can be used in an environment where the ambient humidity never exceeds an amount that would cause the oxygen-enriched gas to become over humidified. However, since many of these devices are used in a patient's home under a variety of environmental conditions, the ambient humidity is difficult to control.

Second, a shunt can be installed so that a portion of the oxygen-enriched gas bypasses the membrane device, and remains at an extremely low humidity. When the streams of oxygen-enriched gas are later remixed, an optimal humidity can be achieved. This system however, requires adjustment by the user to match ambient conditions as well as requiring additional valves and tubing.

Porous Media teaches against being able to control the humidity of the patient gas with the use of the HUMIDI-FLOW membrane gas humidifier, and teaches that it is not possible to create higher levels of humidity on the outlet of the HUMIDIFLOW membrane gas humidifier than the atmospheric air, their concern being condensation or "rain out." Porous Media views condensation as harmful: "However, if the oxygen-enriched air stream exiting membrane device 63 were allowed to cool to ambient temperature to enable a patient to breathe the oxygen-enriched air, harmful condensation can occur."

The Spearman patent indicates that: "FIG. 4 shows an embodiment of the oxygen concentrator 92 of the present invention. Oxygen concentrator 92 uses a membrane device 63 similar to the membrane device shown in FIG. 2, but with the first inlet 44 of the membrane device 63 in fluid communication with the outlet 39 of the inlet filter 37 and the first outlet 45 of the membrane device 63 in fluid communication with the inlet 41 of the compressor 40."

Thus, the same stream of air is passed through the membrane device 63 from the first inlet 44 to the first outlet 45 as shown in FIG. 2, but the stream of air is now at approximately ambient pressure and thus at nominally the same pressure as the oxygen-enriched gas passing from the second inlet 61 to the second outlet 62 of the membrane device 63.

This means that the partial pressure of water in the oxygen-enriched gas exiting at the second outlet 62 of the membrane device 63 should be no greater than the partial pressure of water in the air entering the membrane device 63 at the first inlet 44 of the membrane device 63 and thus no greater than the ambient partial pressure of water. As a result, as the oxygen-enriched gas cools on the way to the patient, condensation is inhibited or eliminated.

Thus, there is no need of a bypass valve as in FIG. 2. Additionally, the Patent Examiner from US application Ser. No. 10/958,973 reaffirmed that the "invention requires equal pressure at both level of humidification of gas to overcome condensation of gas at the second level of humidification gas . . . " The provisional patent states "In one embodiment . . . unlike devices in the previous art, the pressure of both the air and the oxygen enriched air streams will be nominally equal to the environmental pressure and thus each other."

From the provisional patent page 3, Porous Media describes the following installation scenarios in which the pressures of oxygen gas and the feed gas are the same: "In this second embodiment the outlet of the compressor is in fluid communication with the inlet of side one of the membrane in the membrane device. The outlet of side one of said membrane device is in fluid communication with the inlet of the oxygen concentration system, which consists of a valve system, adsorption beds, and usually a buffer tank. The outlet of said oxygen concentration system is in fluid communication with side two of the membrane in said membrane device.

The outlet of side two of said membrane device is in fluid communication with, in seriatim, the gas pressure regulator, the flow control valve, and the patient. In this second embodiment both the air and the oxygen-enriched stream are at nominally the same pressure which is higher than the ambient pressure. Like the first embodiment, this second embodiment is different from prior art since there is no total pressure gradient across the membrane."

Porous Media establishes the difference between their device that operates at equal pressures and the Burioka device which is at unequal pressures. Further, Porous Media illustrates the importance of their invention operating at equal pressures and teaches away from pressure gradients: "It is sometimes thought by those experienced in the art that a total pressure gradient across the membrane is required to produce flux across the membrane, suggesting that the module would need to be installed as in FIG. 2 to function, but this is not the case. Since flux across the membrane is caused by a partial pressure gradient of a compound in the respective streams, and the oxygen enriched air enters the membrane device 8 at entrance 10 extremely dry, there is still a partial pressure gradient of water to drive the membrane flux even though the total pressure on the 2 sides of the membrane is nominally equal."

Porous Media indicates in the patent "no matter how the membrane is designed, or how large it is, or how permeable the membrane is to water vapor, the partial pressure of water in the exiting oxygen enriched stream can never be greater than the partial pressure of water in the entering air stream" (to the compressor that is).

SUMMARY OF THE INVENTION

An embodiment of the invention is directed to a membrane oxygen humidifier that is associated with a gas source for increasing humidity of the gas. The membrane oxygen humidifier includes an enclosure, a membrane unit and a humidification source.

The enclosure includes inlet port and an outlet port. The membrane unit is removably mounted in the enclosure to extend between the inlet port and the outlet port. The humidification source is in communication with the enclosure and the membrane unit.

An embodiment of the invention is directed to an oxygen delivery system that includes an oxygen source, a membrane oxygen humidifier, a patient interface, a first tubing and a second tubing. The oxygen source includes an outlet port and an enclosure.

The membrane oxygen humidifier is mounted with respect to the enclosure. The membrane oxygen humidifier includes an enclosure and at least one water permeable membrane. The enclosure has an inlet port and an outlet port. The at least one water permeable membrane extends between the inlet port and the outlet port.

The first tubing interconnects the oxygen concentrator outlet port and the enclosure inlet port. The second tubing interconnects the enclosure outlet port and the patient interface.

Another embodiment of the invention is directed to a method of providing a source of breathable humidified oxygen gas. A membrane oxygen humidifier is provided that includes an enclosure having an inlet port and an outlet port. A membrane unit is removably mounted in the enclosure to extend between the inlet port and the outlet port.

A first gas containing oxygen is directed through the membrane unit. A second gas is directed into the enclosure so that the second gas is in communication with the first gas through the membrane unit. The first gas is humidified by transferring moisture through the membrane unit from the second gas to the first gas.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

FIG. 9 is a perspective view of the membrane unit moving into engagement with a mounting structure in the membrane oxygen humidifier.

FIG. 10 is a perspective view of the membrane unit in engagement with the mounting structure in the membrane oxygen humidifier.

DETAILED DESCRIPTION OF THE PREFERRED EMBODIMENTS

Figure 1:
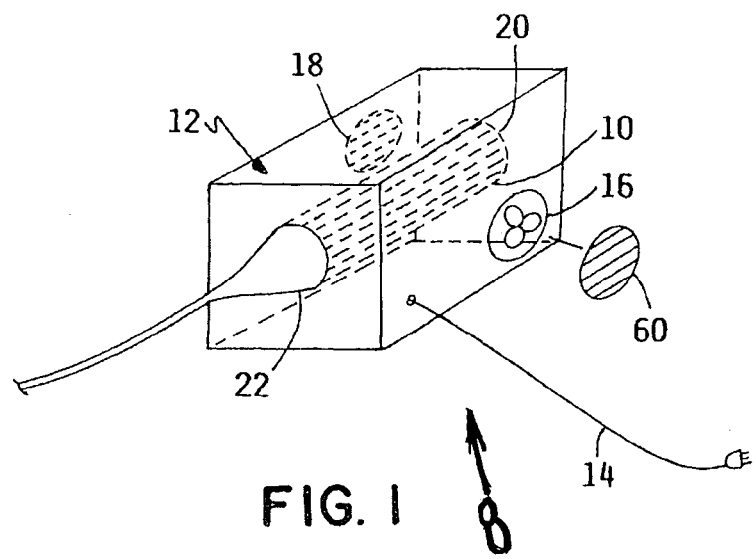
FIG. 1 is a perspective view of a membrane oxygen humidifier according to an embodiment of the invention.

It is desirable to maintain a static level of atmospheric humidity (or as close to static as possible) going into the air compressor while increasing the humidity provided to the patient to preferably high levels of humidity, such as in the range of 40%-65%.

This invention can control higher level of humidity to the patient while imputing no deleterious effect to the concentrator. It is also desirous to provide an easy to install membrane humidifier to an oxygen concentrator that does not require altering of manufacturers' equipment as this could lead to problems for the patient, the provider and the OEM of the concentrator. It is also a desire to be able to test the oxygen performance of the machine with the membrane humidifier installed without having to use a secondary filter-dryer.

The present invention is novel and accomplishes all of the desired performance characteristics of the prior art yet without having to alter the manufacturer's equipment, it provides a simple installation procedure that can be performed inside of 30 seconds (even by an elderly patient), increases the safety of the device, provides a much more efficient and economical means for verifying oxygen performance and also allows the patient to have high levels of humidity without damaging their home or oxygen concentrator.

The hollow fiber membrane 10 may be selected to permit water vapor to pass there through while other gases such as oxygen and nitrogen are hindered from passing there through. Since the oxygen-enriched gas entering the hollow fiber membrane 10 at inlet 20 is extremely dry, there exists a driving force for water vapor to pass across the selective membrane.

Through this process, the humidity of the oxygen-enriched gas is higher when the oxygen-enriched gas exits the hollow fiber membrane 10 at outlet 22 than when the oxygen-enriched gas enters the hollow fiber member 10 at inlet 20. While the membrane selectivity is high, the oxygen level is changed only by dilution with water vapor.

An embodiment of the invention is directed to a membrane oxygen humidifier 8, as illustrated in the figures. The membrane oxygen humidifier 8 may include at least one hollow fiber membrane 10 within an enclosure 12. The hollow fiber membrane 10 has an inlet 20 and an outlet 22.

In this configuration, the membrane oxygen humidifier 8 is in fluid communication with the tubing downstream of sieve towers in the oxygen concentrator 34. This configuration does not utilize sweep gas from the inlet of the oxygen concentrator in conjunction with the humidification process.

A fan 16 may be used to direct the air across the membranes 10. It is possible to use other techniques for directing air across the membranes 10. Examples of such other techniques include a compressor, a vacuum and a component attached to a home ventilation system.

To enhance the usable life of the membrane oxygen humidifier 8, the hollow fiber membrane 10 may be removably mounted in the enclosure 12. Such a configuration would enable the hollow fiber member 10 to be replaced if the hollow fiber membrane is damaged or contaminated.

An electrical plug 14 may be provided to provide power to the fan 16. Alternatively or additionally, the membrane oxygen humidifier 8 may include a re-chargeable battery for a portable version of the invention so that the patients can connect the device to their portable oxygen tanks.

The membrane oxygen humidifier 8 may also include at least one filter 18. One filter 18 is located at the air inlet of the device and one filter is located at the air outlet of the device. The reason for employing the filters is that most patients on oxygen concentrators are smokers and the smoke from the cigarettes can contaminate and coat the membranes 10, potentially degrading the performance of the membrane oxygen humidifier 8.

Figure 2:
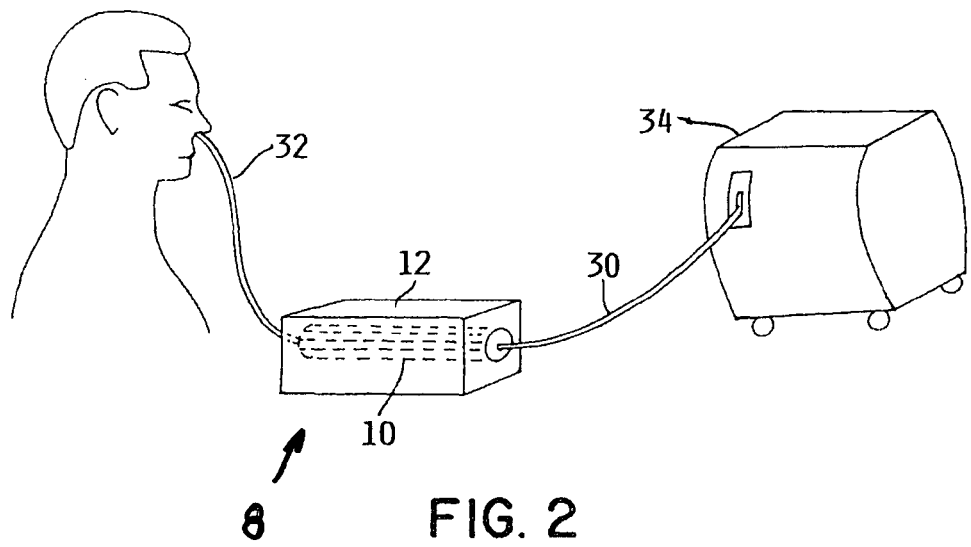
FIG. 2 is a perspective view of the membrane oxygen humidifier used in conjunction with a patient breathing circuit.

Installation of the novel invention is as easy as connecting the adapting oxygen tubing 30 to an oxygen concentrator 34, as illustrated in FIG. 2. Then an oxygen tube 30 with nasal cannula 32 is connected to the patient. To operate the device, one simply plugs the membrane oxygen humidifier 8 into an electrical outlet and turns the unit "on" using the "on/off" switch 24. To turn the humidification off, the patient can simply press the "off" button on the "on/off" switch 24. Once the unit is turned on, the fan 16 blows at a predetermined flow rate that can also be adjusted from about 1 lpm to 100 lpm.

Figure 3:
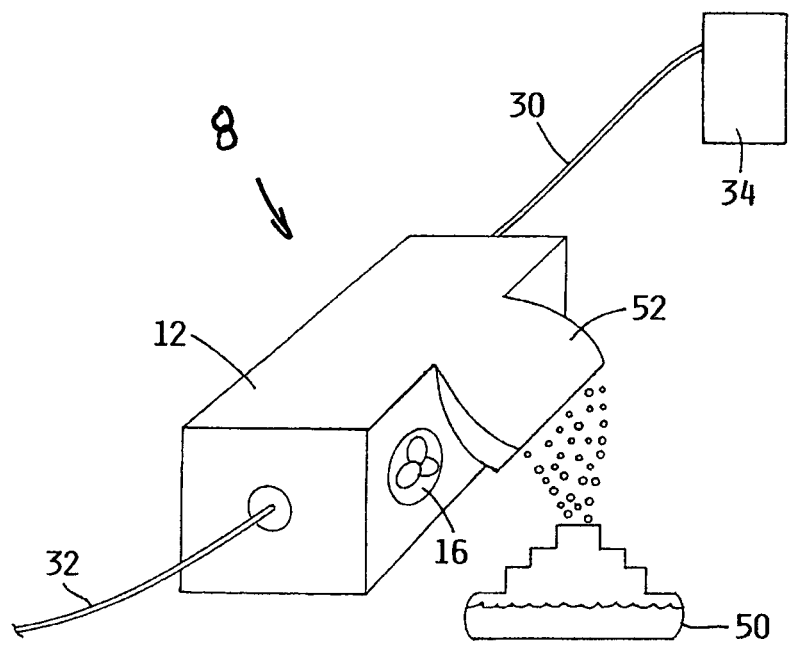
FIG. 3 is a perspective view of the membrane oxygen humidifier used adjacent to a room air humidifier.
Figure 4:
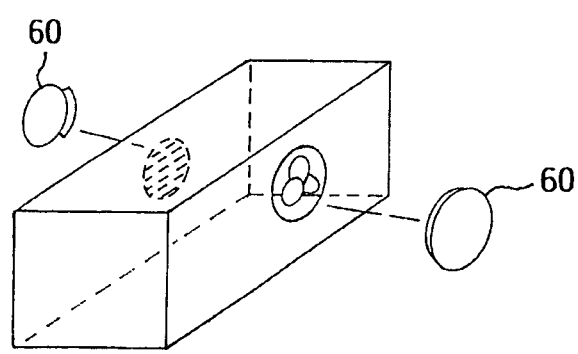
FIG. 4 is a perspective view of caps removable mounted to the membrane oxygen humidifier.

The present invention also provides a technique to increase the humidity levels to the patient higher than the inlet ambient air to the compressor by allowing the patient the ability to place a humidifier 50 proximate to the inlet of the fan 16 and adjust the flow rate to be close to the flow rate of the saturated air that has been humidified proximate to the humidifier, as illustrated in FIG. 3.

To increase the portion of the humidity that is directed from the humidifier 50 to the membrane oxygen humidifier 8, a hood 52 may be provided on at least one of the humidifier 50 and the membrane oxygen humidifier 8 to contain and direct the humidified air directly into the fan 16 of the membrane oxygen humidifier 8.

The membrane oxygen humidifier 8 may be connected to a long tube of between about 50-100 feet in length and can be located this far from the oxygen concentrator. The membrane oxygen humidifier 8 can be put into a small humidifying chamber that is isolated from the oxygen concentrator.

An oxygen tube can then be connected from the humidifier to a patient who can be as far as 50 feet away from the membrane oxygen humidifier. With this means of supplemental humidification, the humidity entering the air compressor will never be substantially higher than ambient, meaning within 10%-20% points.

The configuration of the membrane oxygen humidifier 8 enables testing of the oxygen concentrator oxygen performance. To test the oxygen concentrator for oxygen performance with the membrane installed, the patient can attach the caps 60 to the membrane oxygen humidifier 8 that seals the air inlet and the outlet orifices 62.

This process allows the oxygen only to flow through the membrane tubes without blowing air across the membrane 10, causing inaccurate readings due to the transfer of moisture (water vapor) across the membranes 10.

To simplify the operation of the membrane oxygen humidifier 8, the caps 60 may be operably connected to the enclosure 12 so that the caps 60 are mechanically moved between open and closed positions. In one configuration, the switch 24 that controls the operation of the fan 16 also controls the movement of the caps 60 between the open and closed positions.

Alternatively, a separate switch may be provided to control movement of the caps 60 between the open and closed position. It is also possible to bias the caps 60 to a closed position and then have the force generated by flow of air from the fan 16 to cause the caps 60 to move from the open position to the closed position.

As an alternative to controlling the operation of the membrane oxygen humidifier 8 separately from the oxygen concentrator 34, it is possible to include a gas flow switch that is positioned at least partially in the path of oxygen enriched gas flowing from the oxygen concentrator 34 such as in tube 30, tube 32 or membrane oxygen humidifier 8.

When the gas flow switch senses movement of gas being generated by the oxygen concentrator 34, the gas flow switch may activate the fan 16. Similarly, when the gas flow switch senses cessation of gas from the oxygen concentrator 34, the gas flow switch may deactivate the fan.

The device is novel as well and operates with substantially unequal pressures on either side of the membrane where the oxygen is at approximately 3-6 psig. Generally, the oxygen is operational at around 3-6 psig. The air directed across the membrane is generally at atmospheric pressure. The operating pressures may also be equal to not limit the scope of the invention.

Alternatively, a tube can be provided with the invention that is in fluid communication with the inlet of membrane humidifier. The air flow across the membrane is generally provided by a fixed speed or variable fan that generally operates at ambient pressure. In another embodiment, a tube is connected from the inlet of the air compressor to the humidifier whereby a suction is pulled on the humidifier drawing the air from the inlet of the humidifier across the membrane.

The humidifier humidifies the oxygen close to the ambient air relative humidity proximate to the inlet of the humidifier which is generally within 10%-20% RH to the ambient air proximate to the humidifier. For example, if the relative humidity proximate to the humidifier is 30%, the RH of the outlet of the humidifier will be around 10%-28%.

Figure 5:
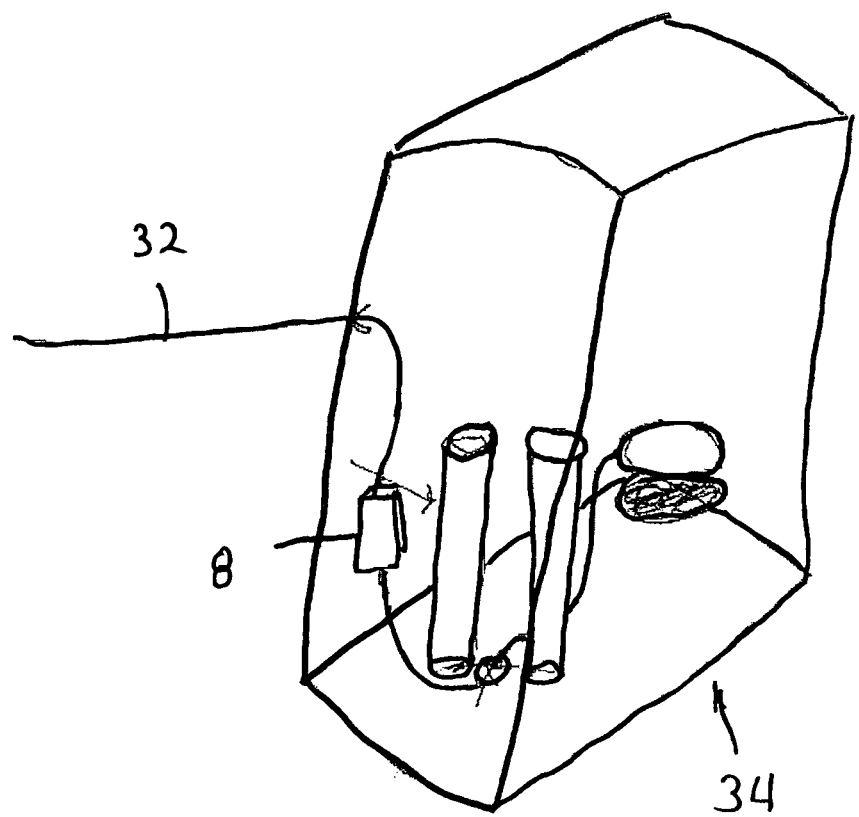
FIG. 5 is a perspective view of the membrane oxygen humidifier mounted inside of an oxygen concentrator.

In another configuration of the invention, the membrane oxygen humidifier 8 may be installed inside of the oxygen concentrator 34, as illustrated in FIG. 5. The inlet port of the membrane oxygen humidifier 8 is connected to the tubing on the downstream side of the sieve bed 36. The outlet connection of the membrane oxygen humidifier 8 is connected to the inlet side of the outlet port of the oxygen concentrator 34.

An advantage of this configuration is that the membrane oxygen humidifier 8 is protected from damage that could result from the membrane oxygen humidifier 8 being mounted separate from the oxygen concentrator 34 such as illustrated in FIG. 2.

Alternatively, the membrane oxygen humidifier 8 may be mounted on an outer surface of the oxygen concentrator 34. In such a configuration, the inlet port of the membrane oxygen humidifier 8 is connected to the outlet port of the oxygen concentrator 34.

An advantage of this configuration is that it is not necessary to obtain access to the interior of the oxygen concentrator 34, which could potentially impact the warranty of the oxygen concentrator 34.

The membrane unit 10 may have a variety of configurations using the concepts of the invention, such as the hollow fiber configuration illustrated in FIGS. 1 and 2, to transport humidity from the atmosphere to the oxygen.

An important criteria in fabricating the membrane unit 10 is to facilitate the greatest amount of humidity transport from the atmosphere to the oxygen while enabling the membrane unit 10 to integrate into the membrane oxygen humidifier 8.

Another criteria in fabricating the membrane unit 10 is to facilitate periodic replacement of the membrane unit 10 in the membrane oxygen humidifier 8 because over time the membrane unit 10 may become contaminated and thereby decrease in efficiency.

Fabricating the membrane unit 10 to facilitate periodic replacement enables the membrane oxygen humidifier 8 to operate at a high efficiency without replacing the entire membrane oxygen humidifier 8 because the cost of the membrane unit 10 may be significantly lower than the cost of the membrane oxygen humidifier 8.

Figure 6:
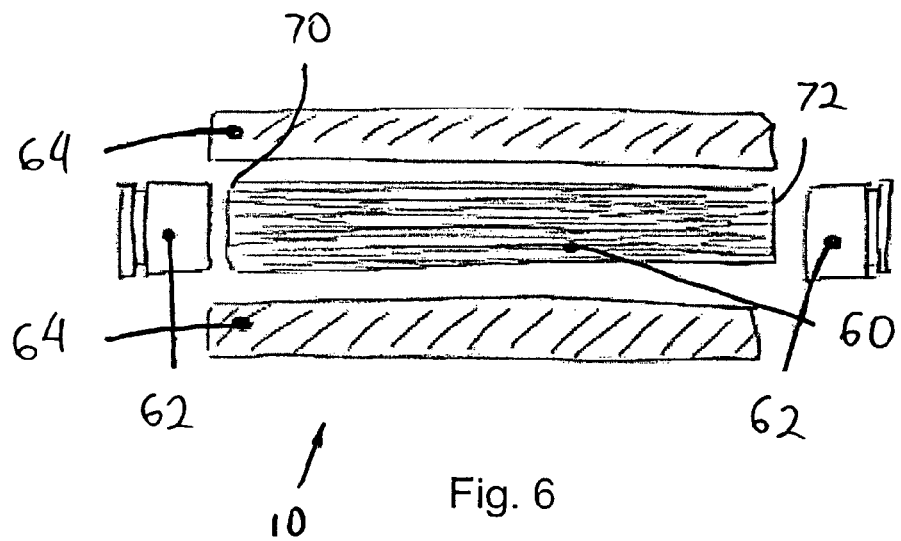
FIG. 6 is an exploded side view of a membrane unit.
Figure 7:
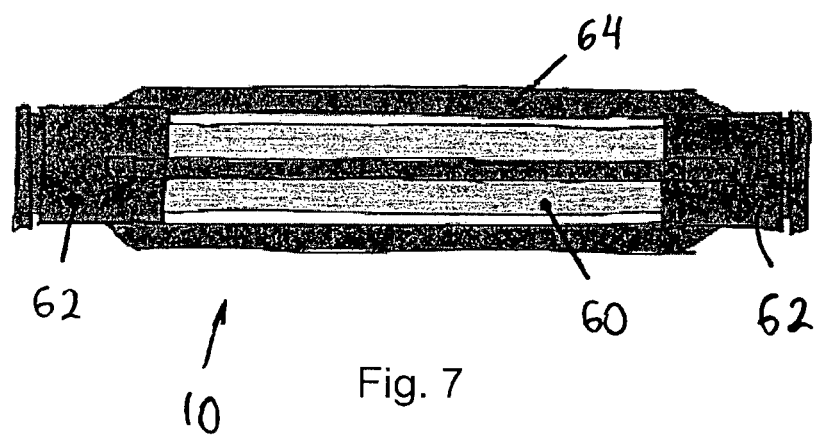
FIG. 7 is a side view of the membrane unit of FIG. 6.
Figure 8:
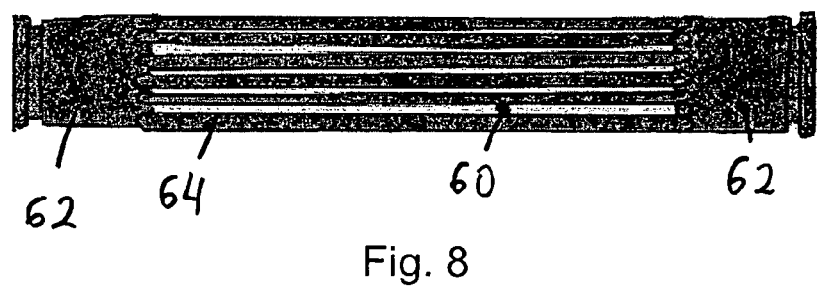
FIG. 8 is a side view of an alternative configuration of the membrane unit.

In certain embodiments, the membrane unit 10 includes a plurality of water vapor permeable membranes 60, a pair of end caps 62 and a membrane unit support structure 64, as illustrated in FIGS. 6-8. The water vapor permeable membranes 60 utilized in this embodiment may include a hollow fiber configuration with an input end 70 and an output end 72. In certain embodiments, the membrane unit 10 is configured so that oxygenated gas from the gas source passes through an inner region of the water vapor permeable membrane 60 and a gas containing water vapor such as air flows across an outer surface of the water vapor permeable membrane.

While the drawings illustrate that the water vapor permeable membranes 60 are oriented in a substantially straight configuration, it is possible to use other configurations for the water vapor permeable membranes 60. For example, the water vapor permeable membranes 60 may be oriented in a U-shaped configuration.

The water vapor permeable membranes 60 may be fabricated from a variety of materials and with a variety of diameters and lengths to provide the membrane unit 10 with a moisture (water vapor) transfer capability. Selection of the water vapor permeable membranes 60 is thereby within the scope of a person of skill in the art.

Proximate each end of the water vapor permeable membranes 60, the end caps 62 are provided. The membrane ends may be potted in the end caps 62 to thereby facilitate passing of the oxygenated air through the membrane oxygen humidifier 8 while substantially eliminating leaking of the oxygenated air. A person of skill in the art will appreciate that there are a variety of suitable techniques for potting the membrane ends in the end caps 62.

The end caps 62 may also include an engagement structure that facilitates attachment of the membrane unit 10 to the other portions of the membrane oxygen humidifier 8. In certain embodiments, the engagement structure includes a flat circular end 80 and a channel 81 that is positioned proximate the flat circular end 80.

The membrane unit support structure 64 extends between the end caps 62. In certain embodiments, the membrane unit support structure 64 is an elongated piece 82 and the opposite ends of the elongated piece 82 are attached to the end caps 62. An example of one suitable technique for attaching the elongated pieces 82 to the end caps 62 is an adhesive.

The elongated pieces 82 are mounted in a spaced-apart configuration around the membrane unit 10. In one such configuration, there are four of the elongated pieces 82 around the membrane unit 10, as illustrated in FIG. 7. In another configuration, there are at least twelve of the elongated pieces 82 around the membrane unit 10, as illustrated in FIG. 8.

An alternative configuration of the invention includes an interlocking fitting provided on the membrane unit 10 and the enclosure. An example of one such interlocking fitting is a snap-fit receptacle, as illustrated in FIGS. 9 and 10. At least one of the end caps 62 includes a tab 90 extending therefrom. In certain embodiments, there are two tabs 90 that extend from each of the end caps 62.

The arm 90 may be fabricated from a resilient material that permits the arm 90 to deflect in response to a force placed thereon. When the force is removed, the arm 90 returns to the initial position. In certain embodiments, the membrane unit 10 may be attached to and detached from the membrane oxygen humidifier 8 using manual force.

In such situations, the arm 90 should have sufficient strength to resist unintentionally disconnecting from the membrane oxygen humidifier 8 while at the same time enabling the membrane unit 10 to be separated from the membrane oxygen humidifier 10 by a person grasping the membrane unit 10 and pulling the membrane unit 10 away from the membrane oxygen humidifier 8.

Proximate a distal end of the arm 90, a tooth 92 extends therefrom. A height of the tooth 92 may be selected in conjunction with the rigidity of the arm 90 because when the height of the tooth 92 is greater, it will be necessary for the arm 90 to deflect further during the process of attaching the membrane unit 10 to the membrane oxygen humidifier 8 as well as when detaching the membrane unit 10 from the membrane oxygen humidifier 8.

While it is illustrated that the snap-fit receptacle is positioned at the end of the membrane unit 10, it is possible for the snap-fit feature to be utilized at other locations on the membrane unit 10. For example, the snap-fit receptacle may be positioned at an intermediate location on the membrane unit 10 that is between the end caps 62.

The membrane oxygen humidifier 10 includes a mounting structure 94 that has a pair of arms 96 extending therefrom. A distal end of each arm 96 has a tooth 98 extending therefrom. In certain embodiments, the teeth 98 may extend towards each other. The teeth 98 may be oriented to engage the teeth 92 on the membrane unit 10 to thereby retain the membrane unit 10 in a stationary position with respect to the mounting structure 94.

An end of the membrane unit 10 may include a sealing mechanism 100 that reduces the potential of oxygenated air from escaping therefrom. In certain embodiments, the sealing mechanism 100 is an O-ring. The O-ring may be at least partially recessed in the end surface of the end cap 62.

Figure 11:
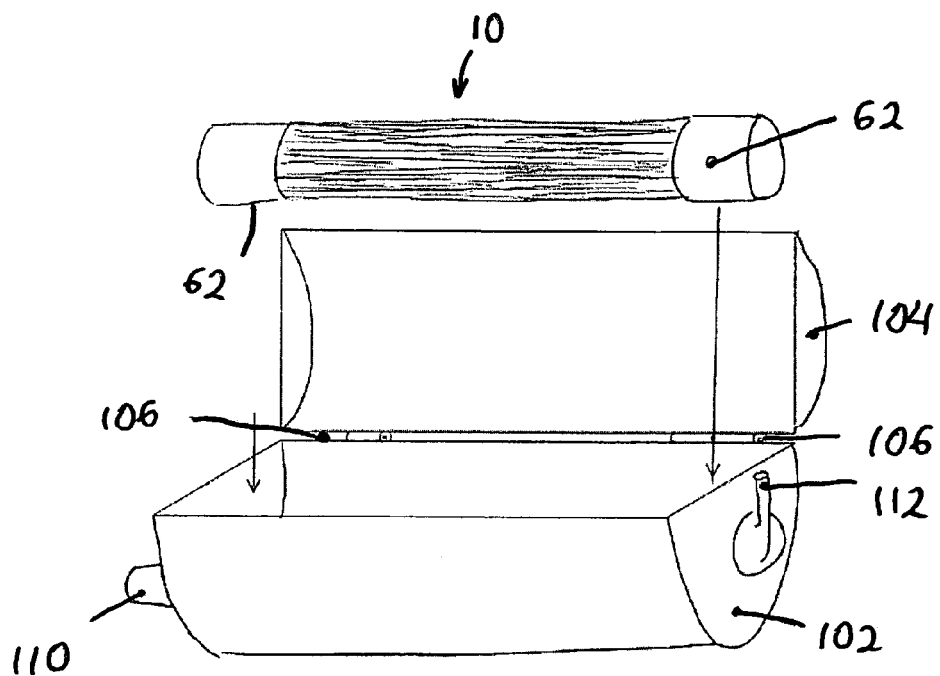
FIG. 11 is a perspective view of an alternative configuration of the membrane unit moving into engagement with the membrane oxygen humidifier.
Figure 12:
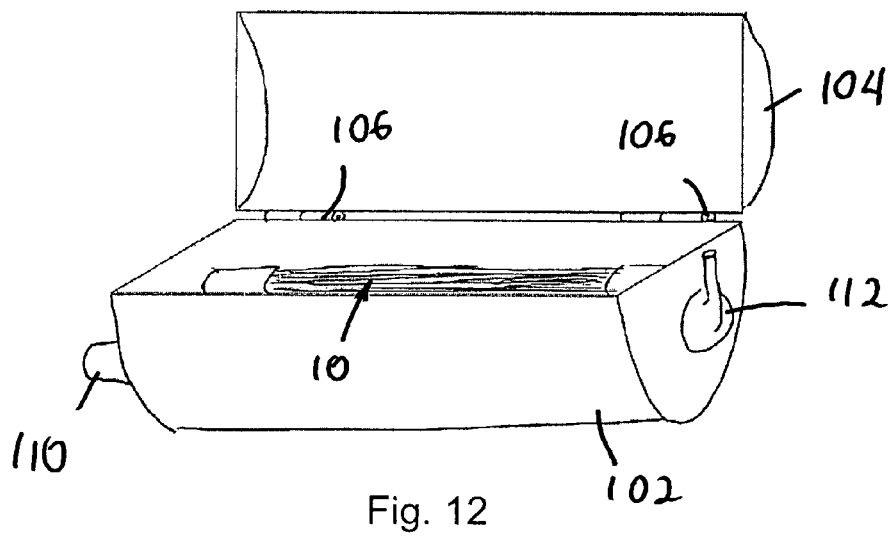
FIG. 12 is a perspective view of the membrane unit in engagement with the mounting structure in the membrane oxygen humidifier.

The membrane oxygen humidifier 10 may have a cylindrical configuration, as illustrated in FIGS. 11 and 12. In this embodiment, the membrane oxygen humidifier 10 may include a body portion 102 and a cap portion 104 that are operably attached to each other.

In one such configuration, the cap portion 104 is operably attached to the body portion 102 with at least one hinge 106, which enables the cap portion 104 to pivot with respect to the body portion 102 to access the membrane unit 10 such as when it is desired to replace the membrane unit 10.

The membrane oxygen humidifier 8 is separated into the body portion 102 and the cap portion 104 along an axis that is generally parallel to an axis of the membrane unit 10. The axis that divides the membrane oxygen humidifier 8 into the body portion 102 and the cap portion 104 may be offset from the axis of the membrane unit 10.

When in use, the cap portion 104 is in a closed configuration with respect to the body portion 102. Pivoting the cap portion 104 to an open configuration with respect to the body portion 102 enables the interior of the membrane oxygen humidifier 10 to be accessed such as to replace the membrane unit 10.

The body portion 102 may include an inlet port 110 and an outlet portion 112. The inlet port 110 is provided at a first end thereof and is used for operably connecting the membrane oxygen humidifier 10 to the oxygen concentrator 34. The outlet port 112 is provided at a second end of the body portion 102 and is used for operably connecting the membrane oxygen humidifier 10 to the patient.

While not illustrated in FIGS. 11 and 12, the membrane oxygen humidifier 10 may include the snap-fit receptacle that is discussed in conjunction with FIGS. 9 and 10. The snap-fit receptacle thereby retains the membrane unit 10 in a stationary position with respect to the membrane oxygen humidifier 8 so that oxygenated air is humidified while passing through the membrane oxygen humidifier 8 prior to being delivered to the patient.

Figure 13:
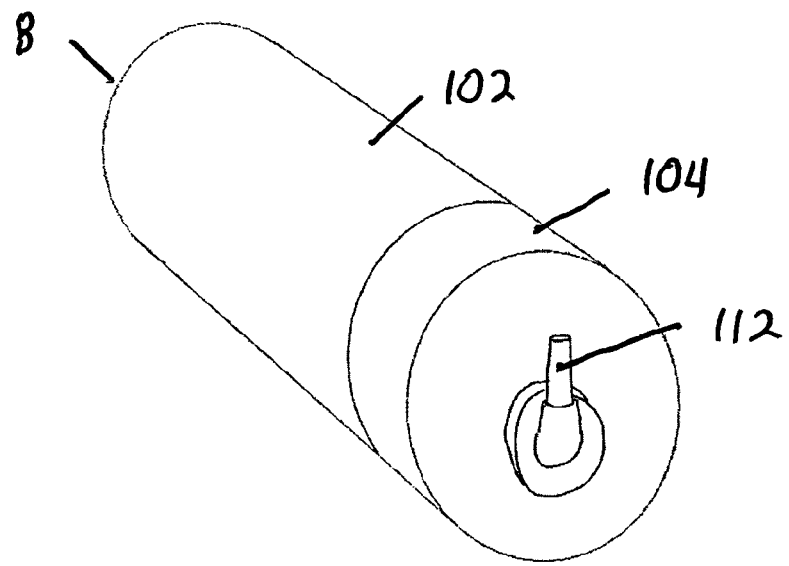
FIG. 13 is a perspective view of an alternative configuration of the membrane oxygen humidifier.
Figure 14:
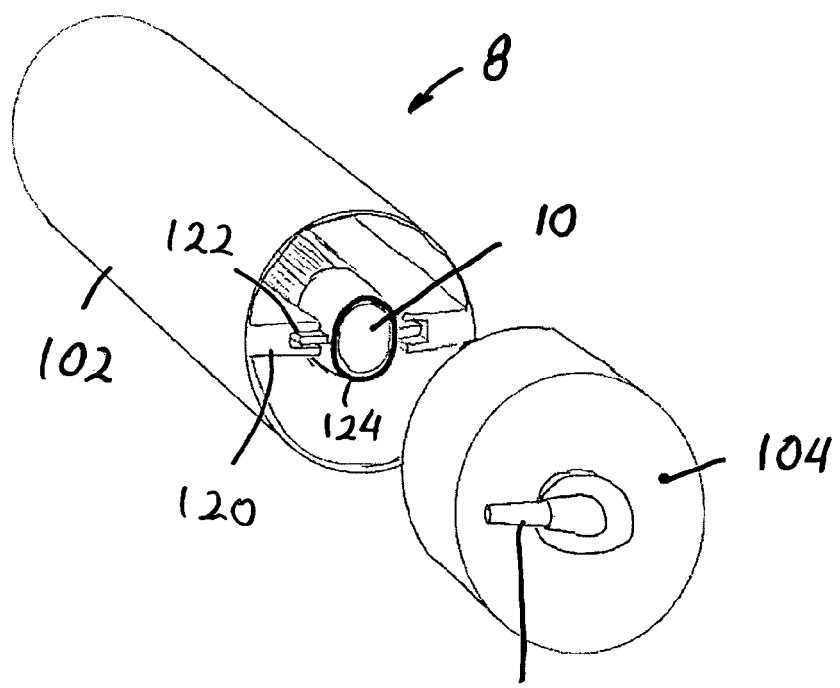
FIG. 14 is an exploded perspective view of the membrane oxygen humidifier of FIG. 13 where a cap portion is separate from a base portion.

Another configuration of the membrane oxygen humidifier 10 is illustrated in FIGS. 13 and 14. In this embodiment, the membrane oxygen humidifier 10 may include a body portion 102 and a cap portion 103 that are operably attached to each other.

The membrane oxygen humidifier 8 is separated into the body portion 102 and the cap portion 104 along an axis that is generally perpendicular to an axis of the membrane unit 10. The axis that divides the membrane oxygen humidifier 8 into the body portion 102 and the cap portion 104 may be proximate to one of the ends of the membrane oxygen humidifier 8. In such a configuration, the base portion 102 may have a height that is approximately the same as the height of the membrane unit 10, as illustrated in FIG. 14.

The body portion 102 may include an inlet port (not shown) and an outlet portion 112. The inlet port is provided at a first end thereof and is used for operably connecting the membrane oxygen humidifier 10 to the oxygen concentrator 34. The outlet port 112 is provided at a second end of the body portion 102 and is used for operably connecting the membrane oxygen humidifier 10 to the patient.

The body portion 102 may include at least one inwardly directed extension 120, as illustrated in FIG. 14. A distal end of the extension 120 may have a channel 122 formed therein that is adapted for use in guiding the membrane unit 10 into the body portion 102. In one such embodiment, the channel 122 may receive the elongated piece 82, which is discussed above.

At least one end of the membrane unit 10 may include a sealing mechanism 124 that reduces the potential of oxygenated air escaping therefrom. In certain embodiments, the sealing mechanism 124 is an O-ring. The O-ring may be at least partially recessed in the end surface of the end cap 62.

Figure 15:
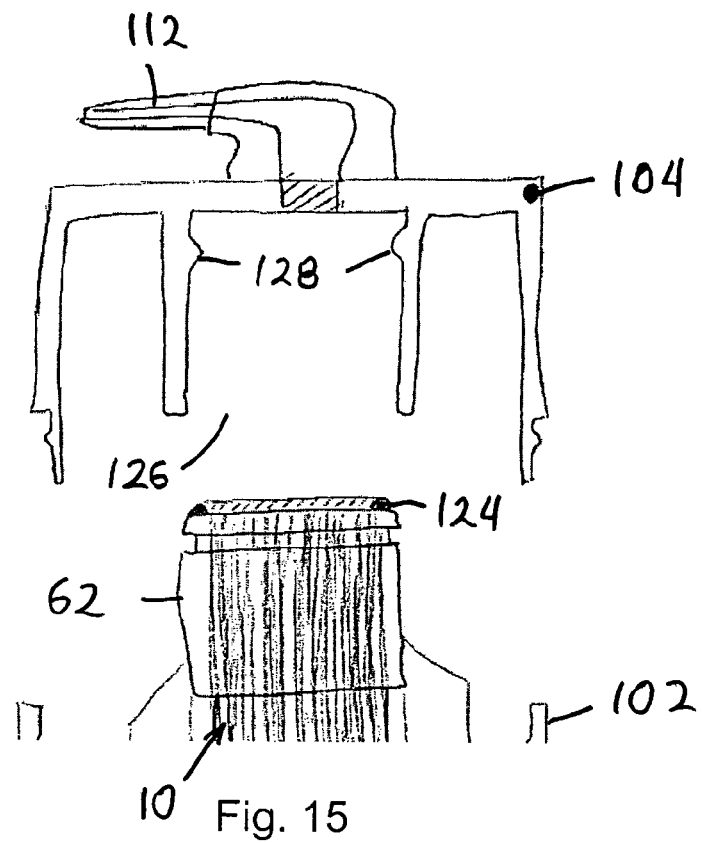
FIG. 15 is a sectional view of the membrane oxygen humidifier of FIG. 13 where the cap portion is separated from the base portion.
Figure 16:
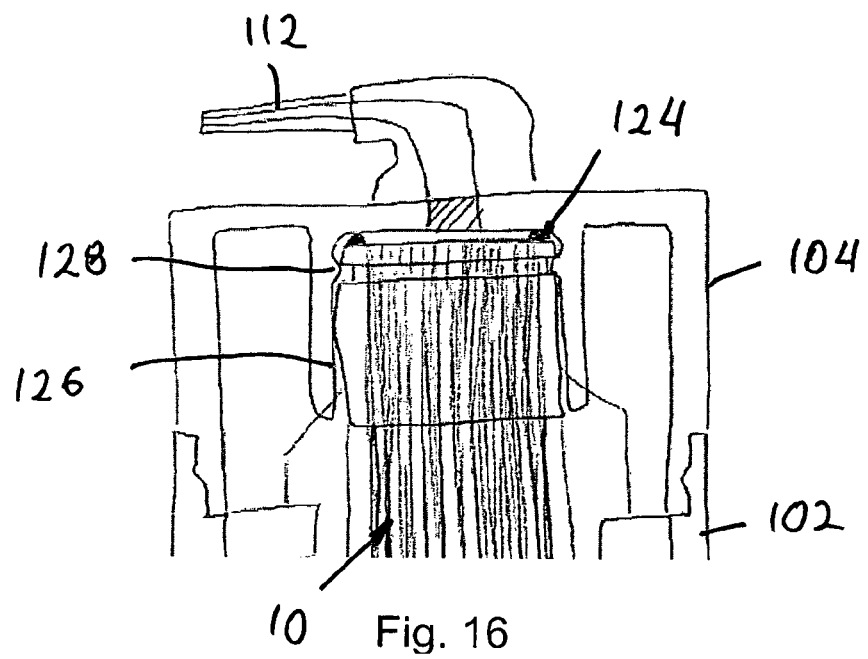
FIG. 16 is a sectional view of the membrane oxygen humidifier of FIG. 13 where the cap portion is in engagement with the base portion.

A variety of techniques may be used to removably attach the cap portion 104 to the body portion 102. An example of one suitable mechanism are complementary threads on the cap portion 104 and the body portion 102, as illustrated in FIGS. 15 and 16.

The cap portion 104 may include a receptacle 126 that facilitates accurately positioning the end of the membrane unit 10 with respect to the cap portion 104. In certain embodiments, the receptacle 126 has a depth that extends over a least a portion of the end cap 62, which is discussed above.

The receptacle 126 may also include an extension 128 that extends from an inner surface thereof. The extension 128 is capable of engaging the channel 81 in the end cap 62 to enhance the ability of forming a seal between the membrane unit 10 and the cap portion 104. This seal may supplement the seal provided by the O-ring.

In the preceding detailed description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

It is contemplated that features disclosed in this application, as well as those described in the above applications incorporated by reference, can be mixed and matched to suit particular circumstances. Various other modifications and changes will be apparent to those of ordinary skill.

The invention claimed is:

1. A membrane oxygen humidifier that is associated with a gas source for increasing humidity of the gas received from the gas source, wherein the membrane oxygen humidifier comprises:
   an enclosure comprising:
      an inlet port;
      an outlet port;
      a body portion that comprises a mounting structure having a pair of arms extending therefrom and wherein each of the arms has a body portion tooth extending therefrom; and
      a cap portion that is mountable with respect to the body portion to define the enclosure;
   a membrane unit that comprises;
      a water vapor permeable membrane having an inner region and an outer surface, wherein oxygenated gas from the gas source is configured to pass through the inner region between the inlet port and the outlet port; and
      a pair of resilient arms extending therefrom, wherein proximate a distal end of each arm, a membrane unit tooth extends therefrom, wherein the arms deflect when the membrane unit is moved towards the body portion so that the body portion teeth engage the membrane unit teeth to form a snap-fit receptacle that removably attaches the membrane unit to the enclosure; and
   a humidification source that is configured to provide a gas containing water vapor to the outer surface of the water vapor permeable membrane.

2. The membrane oxygen humidifier of claim 1, wherein the membrane unit is removably mounted in the enclosure.

3. The membrane oxygen humidifier of claim 1, wherein the cap portion is pivotally mounted to the body portion to move between an open configuration and a closed configuration.

4. The membrane oxygen humidifier of claim 1, wherein the gas containing water vapor is air.

5. The membrane oxygen humidifier of claim 1, wherein the membrane unit comprises:
   a plurality of water vapor permeable membranes that each have a first end and a second end;
   a first end cap mounted proximate the first ends of the membranes; and
   a second end cap mounted proximate the second ends of the membranes; and
   a membrane support structure that extends between the first end cap and the second end cap, wherein the membrane support structure has at least one opening that is configured to allow the gas containing water vapor to pass therethrough.

6. The membrane oxygen humidifier of claim 5, wherein each of the water vapor permeable membranes comprises a hollow fiber membrane, a spiral wound membrane or combination thereof.

7. The membrane oxygen humidifier of claim 1, and further comprising:
 a fan mounted to the enclosure; and
 a battery operably attached to the fan.

8. An oxygen delivery system comprising:
 an oxygen source comprising an inlet port, an outlet port and an enclosure;
 a membrane oxygen humidifier mounted with respect to the oxygen source, wherein the membrane oxygen humidifier comprises:
  an enclosure comprising:
   an inlet port that is operably connected to the oxygen source outlet port;
   an outlet port;
   a body portion that is capable of receiving the membrane unit, wherein the body portion comprises a mounting structure having a pair of arms extending therefrom and wherein each of the arms has a body portion tooth extending therefrom; and
   a cap portion that is mountable with respect to the body portion to define the enclosure; and
  a water vapor permeable membrane unit that extends between the enclosure inlet port and the enclosure outlet port, wherein the water vapor permeable membrane unit comprises:
   at least one water vapor permeable membrane comprises an outer surface and an inner region; and
   a pair of resilient arms extending therefrom, wherein proximate a distal end of each arm, a membrane unit tooth extends therefrom, wherein the arms deflect when the membrane unit is moved towards the body portion so that the body portion teeth engage the membrane unit teeth to form a snap-fit receptacle that removably attaches the membrane unit to the enclosure; and
 a humidification source that is capable of providing water vapor to the outer surface of the at least one water vapor permeable membrane;
 a patient interface; and
 a first tubing interconnecting the enclosure outlet port and the patient interface, wherein the oxygen delivery system is configured to deliver oxygen-containing gas to the patient interface having a humidity level that is higher than a humidity of oxygen-containing gas received at the oxygen source inlet port.

9. The oxygen delivery system of claim 8, wherein the oxygen source is an oxygen concentrator.

10. The oxygen delivery system of claim 8, wherein the at least one water vapor permeable membrane comprises a hollow fiber membrane, a spiral wound membrane or combination thereof.

11. The oxygen delivery system of claim 8, wherein the patient interface is a nasal cannula.

12. The oxygen delivery system of claim 8, wherein the membrane oxygen humidifier is mounted to an outer surface of the oxygen source enclosure.

13. A method of providing a source of breathable humidified oxygen gas, wherein the method comprises:
 providing a membrane oxygen humidifier comprising an enclosure having an inlet port and an outlet port, wherein the enclosure comprises a body portion and a cap portion, wherein the body portion comprises a mounting structure having a pair of arms extending therefrom, wherein each of the arms has a body portion tooth extending therefrom and wherein the cap portion is mountable with respect to the body portion to define the enclosure;
 mounting a membrane unit in the enclosure to extend between the inlet port and the outlet port, wherein the membrane unit comprises a water vapor permeable membrane and a pair of resilient arms, wherein the water vapor permeable membrane has an inner region and an outer surface, wherein oxygenated gas from the gas source is configured to pass through the inner region between the inlet port and the outlet port, wherein the pair of resilient arms extends from the membrane unit, wherein proximate a distal end of each arm, a membrane unit tooth extends therefrom;
 deflecting the arms when the membrane unit is moved towards the body portion so that the body portion teeth engage the membrane unit teeth to form a snap-fit receptacle that removably attaches the membrane unit to the enclosure;
 directing a first gas containing oxygen through the membrane unit;
 directing a second gas into the enclosure so that the second gas is in communication with the first gas through the membrane unit; and
 humidifying the first gas by transferring water vapor through the membrane unit from the second gas to the first gas; and
 removing the membrane unit from the enclosure.

14. The method of claim 13, wherein at least a portion of the enclosure is porous to water vapor from the humidification source.

15. The method of claim 13, and further comprising:
 delivering an oxygen-containing gas to an oxygen concentrator, wherein the oxygen-containing gas has a first moisture concentration; and
 passing the oxygen-containing gas through an oxygen concentrator to increase an oxygen concentration of the oxygen-containing gas, wherein after humidifying, the first gas has a moisture content that is higher than the first moisture concentration.

\* \* \* \* \*